US012618085B2

(12) United States Patent
Ropars et al.

(10) Patent No.: US 12,618,085 B2
(45) Date of Patent: May 5, 2026

(54) OPTIMIZED IBE FERMENTATION METHOD FOR UPGRADING ACETONE

(71) Applicant: IFP Energies Nouvelles, Rueil-Malmaison (FR)

(72) Inventors: Marcel Ropars, Rueil-Malmaison (FR); Nicolas Lopes Ferreira, Rueil-Malmaison (FR); Sandra Menir, Rueil-Malmaison (FR); Helena Gonzalez Penas, Rueil-Malmaison (FR); Eszter Toth, Rueil-Malmaison (FR); Vincent Coupard, Rueil-Malmaison (FR)

(73) Assignee: IFP ENERGIES NOUVELLES, Rueil Malmaison (FR)

( * ) Notice: Subject to any disclaimer, the term of this patent is extended or adjusted under 35 U.S.C. 154(b) by 443 days.

(21) Appl. No.: 18/013,427

(22) PCT Filed: Jun. 17, 2021

(86) PCT No.: PCT/EP2021/066513
§ 371 (c)(1),
(2) Date: Dec. 28, 2022

(87) PCT Pub. No.: WO2022/002624
PCT Pub. Date: Jan. 6, 2022

(65) Prior Publication Data
US 2023/0265464 A1      Aug. 24, 2023

(30) Foreign Application Priority Data
Jun. 29, 2020      (FR) ...................................... 2006785

(51) Int. Cl.
*C12P 7/16*          (2006.01)
*C12P 7/06*          (2006.01)
(52) U.S. Cl.
CPC .. *C12P 7/16* (2013.01); *C12P 7/06* (2013.01)
(58) Field of Classification Search
CPC .... C12P 7/16; C12P 7/06; C12P 7/065; C12P 7/04; Y02E 50/10
See application file for complete search history.

(56) References Cited

U.S. PATENT DOCUMENTS

| | | | |
|---|---|---|---|
| 5,081,321 A | 1/1992 | Fukuhara et al. | |
| 6,930,213 B1 | 8/2005 | Pompetzki et al. | |
| 10,961,489 B2 * | 3/2021 | Coupard ................ | B01D 3/002 |
| 11,946,067 B2 * | 4/2024 | Lopes Ferreira .... | C12N 15/113 |
| 2008/0293125 A1 * | 11/2008 | Subbian .................... | C12P 7/04 |
| | | | 435/254.11 |

| | | |
|---|---|---|
| 2011/0218367 A1 | 9/2011 | Morizane et al. |
| 2019/0203162 A1 | 7/2019 | Coupard et al. |
| 2021/0340480 A1 | 11/2021 | Gonzalez Penas et al. |

OTHER PUBLICATIONS

Charubin et al., Direct cell-to-cell exchange of matter in a synthetic Clostridium syntrophy enables CO2 fixation, superior metabolite yields, and an expanded metabolic space. Metabol. Engineering., 2019, vol. 52: 9-19. (Year: 2019).*
Chen et al., Novel distillation process for effective and stable separation of high-concentration acetone-butanol-ethanol mixture from fermentation-pervaporation integration process. Biotechnol Biofuels., 2018, vol. 11: 286, pp. 1-13. (Year: 2018).*
Youn et al., Effective isopropanol-butanol (IB) fermentation with high butanol content using a newly isolated *Clostridium* sp. A1424. Biotechnol. Biofuels., 2016, vol. 9:230, pp. 1-15. (Year: 2016).*
Survase et al., Membrane assisted continuous production of solvents with integrated solvent removal using liquid-liquid extraction. Bioresource Technol., 2019, vol. 280: 378-386. (Year: 2019).*
Carla Ferreira Dos Santos Vieira et al: "Acetone-free biobutanol production: Past and recent advances in the Isopropanol-Butanol-Ethanol (IBE) fermentation", Bioresource Technology, vol. 287, May 6, 2019 (May 6, 2019), Amsterdam, NL, pp. 121425, XP055627009, ISSN: 0960-8524, DOI: 10.1016/j.biortech.2019. 121425 (ABST).
Karthikeyan D. Ramachandriya et al: "Reduction of acetone to isopropanol using producer gas fermenting microbes", Biotechnology and Bioengineering, vol. 108, No. 10, Jun. 16, 2011 (Jun. 16, 2011), pp. 2330-2338, XP055115054, ISSN: 0006-3592, DOI: 10.1002/bit.23203 (ABST).
Survase Shrikant A et al: "Continuous production of isopropanol and butanol usingDSM 6423", Applied Microbiology and Biotechnology, Springer Berlin Heidelberg, Berlin/Heidelberg, vol. 91, No. 5, May 15, 2011 (May 15, 2011), pp. 1305-1313, XP037013572, ISSN: 0175-7598, [retrieved on May 15, 2011], DOI: 10.1007/ S00253-011-3322-3 (Abst).
International Search Report PCT/EP2021/0066513 dated Sep. 13, 2021 (pp. 1-2).

* cited by examiner

*Primary Examiner* — Ganapathirama Raghu
(74) *Attorney, Agent, or Firm* — Millen, White, Zelano & Branigan, P.C.; Jennifer L. King

(57)          ABSTRACT

The present invention relates to a process for producing alcohols comprising:
  a. an IBE-type fermentation step in at least one bioreactor (R1) in the presence of a natural strain microorganism, and fed at least with an aqueous solution (1) of C5 and/or C6 sugars and a recycled acetone stream (3), in order to produce fermentation gases and a fermentation broth containing fermentation products;
  b. a step of recovering the fermentation products, in order to obtain a stream of fermentation products (2);
  c. a step of treating the stream of fermentation products comprising an acetone separation section in order to produce at least an acetone effluent (3) and an aqueous alcohol effluent (4);
  d. a step for recycling at least a fraction of the acetone effluent (3) from step c) to step a).

17 Claims, 1 Drawing Sheet

OPTIMIZED IBE FERMENTATION METHOD FOR UPGRADING ACETONE

TECHNICAL FIELD

Figure 1:
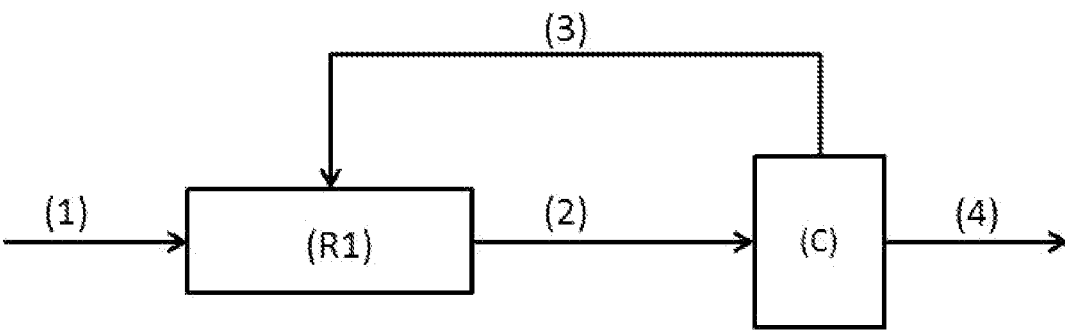

The present invention relates to a process for producing alcohols comprising the IBE fermentation of an aqueous solution comprising C5 and/or C6 sugars in the presence of natural microorganisms, making it possible to maximize the yield of alcohols, in particular of isopropanol.

PRIOR ART

In order to meet the energy transition challenges, considerable research is being conducted to develop "green" processes, affording access to chemical intermediates in an alternative manner to petroleum refining and/or petrochemistry.

Alcohols derived from fermentation (ethanol, n-butanol, denoted butanol hereinafter, isopropanol) are the most promising replacements for petrochemical derivatives. ABE (Acetone—Butanol—Ethanol) fermentation is one of the oldest fermentations to have been industrialized (at the start of the 20th century) and has since been extensively studied (cf. Moon et al. "One hundred years of clostridial butanol fermentation." FEMS Microbiol Lett. 2016 February, 363, 3). There is also IBE (Isopropanol—Butanol—Ethanol) fermentation which produces a mixture of isopropanol, butanol and ethanol (cf. Dos Santos Vieira et al. "Acetone-free biobutanol production: Past and recent advances in the Isopropanol-Butanol-Ethanol (IBE) fermentation." Bioresour Technol. 2019 September, 287:121425). These two types of fermentations are carried out under strict anaerobiosis by a fermentation microorganism generally of the genus *Clostridium*.

These "solventogenic" non-pathogenic strains of Clostridia, used in biotechnology, naturally have the ability to convert a large variety of sugars in order to produce chemical species of interest, and more particularly a mixture of acetone, butanol and ethanol during ABE fermentation (Jones et al. "Acetone-butanol fermentation revisited." Microbiol Rev 1986, 50: 484-524). Some are themselves capable of producing a mixture of isopropanol, butanol and ethanol during an IBE fermentation (Chen et al., "Acetone-butanol-isopropanol production by *Clostridium beijerinckii* (synonym, *Clostridium butylicum*)." Biotechnol Lett 1986, 8: 371-376; George et al., "Acetone, Isopropanol and Butanol Production by *Clostridium beijerinckii* (syn. *Clostridium butylicum*) and *Clostridium aurantibutyricum*." Appl Environ Microbiol 1983, 45: 1160-1163).

Only a few particular solvantogenic strains of Clostridia are naturally capable of producing isopropanol during the fermentation process as an almost total replacement for acetone, in particular certain strains of *Clostridium beijerinckii* (or *C. beijerinckii*), such as strain DSM6423. The other strains produce an Acetone/Butanol/Ethanol (A/B/E) mixture.

During the IBE fermentation process which leads to the Isopropanol/Butanol/Ethanol (I/B/E) alcohol mixture, acetone is therefore an intermediate product of the fermentation production pathway of isopropanol (Máté de Gérando et al., "Genome and transcriptome of the natural isopropanol producer *Clostridium beijerinckii* DSM6423" BMC Genomics, 2018 19:242; Collas, 2012, "Production of isopropanol, butanol and ethanol by metabolic engineered Clostridia", Doctoral thesis in Microbiology and Molecular Biology, AgroParisTech, France). However, at the end of IBE fermentation, carried out by the DSM6423 strain for example, the fermentation broth obtained systematically comprises acetone, often at a low concentration (generally around 2% of the mass of the solvents produced). This presence of acetone in the products of an IBE fermentation process is however characteristic of a yield of alcohols, in particular of isopropanol, which may be incomplete.

It then appears useful, in order to make the large-scale fermentation production of I/B/E alcohols economically advantageous, to optimize conventional IBE fermentation processes by converting the co-produced acetone to alcohol, in particular to isopropanol, thus making it possible to limit the accumulation of this acetone by-product in the processes. Recovering and converting the acetone also makes it possible to upgrade it and especially to improve the sugar to alcohol conversion yields.

Industrial processes for converting acetone to isopropanol by chemical means exist. These are conventional catalytic hydrogenation processes under pressure. For example, the processes described in documents EP 0379323 and US 2011/0218367 are processes for producing isopropanol by reaction of acetone with hydrogen in the presence of catalysts based on hydrogenating metal, in particular based on Raney nickel, at a temperature between 20° C. and 200° C. and a pressure between 1 and 80 bar (cf. EP 0379323). Application US 2011/0218367 specifies that the isopropanol selectivity is improved in the presence of water. U.S. Pat. No. 6,930,213 itself describes a process for the hydrogenation of acetone to isopropanol in several reaction stages so as to produce high-purity isopropanol with an improved selectivity.

At the same time, the enzymatic pathway for converting acetone is explored. The literature describes, for example, the reduction of acetone to isopropanol using a particular strain of *Clostridium*, notably the strain *Clostridium ragsdalei*, in a fermentation system very different from IBE or ABE fermentation, since it consists of the fermentation of a gaseous substrate resulting from gasification, also called syngas, which comprises a gaseous mixture of nitrogen $N_2$, hydrogen $H_2$, carbon dioxide $CO_2$ and carbon monoxide CO (Ramachandriya K D et al., "Reduction of acetone to isopropanol using producer gas fermentation microbes", Biotechnol Bioeng., 2011 October, 108(10), 2330-8). In this process, acetone is added to the fermentation medium, at concentrations ranging up to 2 g/l without affecting the growth of the microorganism.

Another study proposes to optimize Acetone—Isopropanol—Butanol fermentation in the presence of a natural strain of *Clostridium*, NJP7, to improve the production of butanol or butanol-isopropanol, notably by introducing exogenous acid (acetic acid or butyric acid) or a precursor of specific enzymes into the culture medium with the glucose (Xin et al., "Strategies for improved isopropanol-butanol production by a *Clostridium* strain from glucose and hemicellulose through consolidated bioprocessing", Biotechnololy for Biofuels, 2017, 10:118). This same study shows that the butanol and isopropanol titers and productivities of the *Clostridium* NJP7 strain can be further improved during a fed-batch fermentation by in situ extraction using biodiesel.

Still other studies propose making genetic modifications to a strain of *Clostridium acetobutylicum* ATCC 824, which naturally produces an Acetone—Butanol—Ethanol mixture, to make it produce isopropanol as a replacement for acetone. However, the production of residual acetone is still observed, despite the presence of an alcohol dehydrogenase produced by the genetically modified microorganism and capable of effectively converting the acetone (Joungmin Lee et al., "Metabolic Engineering of *Clostridium acetobutyli-cum* ATCC 824 for Isopropanol-Butanol-Ethanol Fermentation", George et al., Applied and Environmental Microbiology, March 2012, Vol. 78 N. 5, p. 1416-1423).

None of these documents proposes a process for producing alcohols by enzymatic conversion of C5 and/or C6 sugars, allowing the direct upgrading of acetone, notably of acetone co-produced with the alcohols. Nor do any of the documents propose a relatively simple process scheme making it possible to substantially improve the sugar to alcohol conversion rate and therefore the yields of alcohols produced, in particular of isopropanol, which represents a significant economic saving.

SUMMARY OF THE INVENTION

The present invention thus relates to a process for producing alcohols comprising the following steps:

a. a fermentation step using a reaction section comprising at least one bioreactor wherein an IBE-type fermentation is carried out in the presence of a strain of *Clostridium*, in particular of industrial interest, said reaction section being fed at least with an aqueous solution of C5 and/or C6 sugars and a recycled acetone stream, in order to produce fermentation gases and a fermentation broth containing fermentation products comprising butanol, ethanol, isopropanol and acetone;
   b. a step of recovering the fermentation products, in order to obtain a stream of fermentation products;
   c. a step of treating the stream of fermentation products from step b) using an acetone separation section in order to produce at least an acetone effluent and an aqueous alcohol effluent;
   d. a step of recycling the acetone which uses at least one transfer section in order to recycle at least one faction of the acetone effluent from step c) to step a), said at least one fraction of the acetone effluent which is transferred constituting said recycled acetone stream which feeds the reaction section of step a).

Surprisingly, the applicant has discovered that it was possible to reintroduce into the fermentation medium, according to a simple process scheme, the acetone co-produced with alcohols by the natural microorganisms, without any particular purification, so as to convert it to isopropanol using these same natural microorganisms. This reassimilation and conversion of the co-product to alcohol, in particular to isopropanol, makes it possible to substantially improve the sugar to alcohol yield, which represents a significant economic saving. The applicant has in fact discovered that the acetone co-produced during the IBE fermentation by natural microorganisms can be easily recycled and almost completely reassimilated by the same microorganisms in order to be converted to isopropanol.

The process according to the invention thus makes it possible to increase the yield of isopropanol by 4% to 6% by weight compared to a prior art process, using the same strain and the same amount of natural microorganisms and, in particular, by using a simple system for recycling the co-produced acetone. The improved performance obtained by means of the process according to the invention appear possible, for limited investment and operating costs.

Another advantage of the present invention lies in the possibility of upgrading the co-produced acetone, but also of converting exogenous acetone, which can be defined, according to the invention, as biocompatible acetone derived from fermentation or chemical processes external to the process of the present invention. It appears in fact that the acetone is converted to isopropanol very well, with conversion rates of up to 90%, by microorganisms naturally producing the isopropanol, butanol and ethanol mixture, even at high concentrations of acetone in the fermentation medium.

DESCRIPTION OF THE EMBODIMENTS

According to the invention, IBE-type fermentation or IBE fermentation is fermentation using microorganisms which enable the conversion of sugars comprising 5 carbon atoms (C5) and/or 6 carbon atoms (C6), solubilized in an aqueous solution, to fermentation products comprising solvents predominantly composed of an Isopropanol—Butanol—Ethanol alcohol mixture. During this IBE fermentation, acetone is co-produced; this solvent represents approximately 2% by weight of the weight of solvents produced. Generally, the fermentation also produces fermentation gases, in particular carbon dioxide ($CO_2$) and hydrogen.

According to the invention, the microorganisms, also called bacteria, used in the fermentation system are strains derived from species of *Clostridium*, in particular of industrial interest, capable naturally, that is to say in the wild state, of producing predominantly the alcohols isopropanol, n-butanol, denoted butanol hereinafter, and ethanol, from sugars containing 5 carbons (C5) or 6 carbons (C6). The term "predominantly" means here, preferably at least 60% by weight, preferentially at least 80% by weight, preferably at least 90% by weight, of the solvents obtained by fermentation. These strains are also called "IBE strains" or "wild IBE strains".

A bacterium capable of producing isopropanol in the wild state, in particular capable of carrying out an IBE fermentation in the wild state, may for example be a bacterium selected from a *C. beijerinckii* bacterium, a *C. diolis* bacterium, a *C. puniceum* bacterium, a *C. aurantibutyricum* bacterium, a *C. butyricum* bacterium, a *C. saccharoperbutylacetonicum* bacterium, a *C. botulinum* bacterium, a *C. drakei* bacterium, a *C. scatologenes* bacterium, a *C. perfringens* bacterium and a *C. tunisiense* bacterium, preferably a bacterium selected from a *C. beijerinckii* bacterium, a *C. diolis* bacterium, a *C. puniceum* bacterium, a *C. aurantibutyricum* bacterium and a *C. saccharoperbutylacetonicum* bacterium. Preferably, a bacterium naturally capable of producing isopropanol, in particular capable of carrying out an IBE fermentation in the wild state, is a *C. beijerinckii* bacterium, preferably a subclade of *C. beijerinckii* selected from DSM 6423, LMG 7814, LMG 7815, NRRL B-593, NCCB 27006, a *C. aurantibutyricum* DSZM 793 or ATCC 17777 bacterium, or a subclade of such a *C. beijerinckii* or *C. aurantibutyricum* bacterium having at least 90%, 95%, 96%, 97%, 98% or 99% identity with the DSM 6423 strain (cf.

Assembly: GCA 900010805.1

The first genomic material of the natural Isopropanol/Butanol/Ethanol producing clostridium strain, *C. beijerinckii* DSM6423, was assembled by de novo sequencing. The physical map, containing a unique chromosome, one plasmid and one bacteriophage was the annotated using the Mage MicroScope platform from Genoscope (France).

Organism: *Clostridium beijerinckii*
   Assembly Name: *C. beijerinckii* DSM 6423
   Assembly Title: *C. beijerinckii* DSM 6423 assembly for *Clostridium beijerinckii*
   Assembly Level: complete genome
   Genome Representation: full
   Accession: GCA 900010805

Total Length: 6410404
Ungapped Length: 6410404
N50: 6383364
Spanned Gaps: 0
Unspanned Gaps: 0
Scaffold Count: 3
Count Contig: 3
Contig N50: 6383364
Contig L50: 1
Contig N75: 6383364
Contig N90: 6383364
Scaf L50: 1
Scaf N75: 6383364
Scaf N90: 6383364
Replicon Count: 3
Count Non Chromosome Replicon: 2
Count Alt Loci Units: 0
Count Regions: 0
Count Patches: 0
ENA-LAST-UPDATED: 2018 Jun. 28

The *C. beijerinckii* bacterium of DSM 6423 subclade is particularly preferred.

Advantageously, the microorganisms used naturally synthesize, during fermentation, a specific enzyme, referred to as secondary alcohol dehydrogenase (sadh), which enables the conversion of acetone to isopropanol in the presence of a co-factor, more particularly in the presence of NADPH (nicotinamide adenine dinucleotide phosphate), this co-factor being produced by the same microorganisms in the presence in particular of glucose. According to the invention, these microorganisms are referred to interchangeably as "microorganisms", "natural strain microorganisms", "strains derived from *Clostridium* species" or else "natural strains" or even "wild strains".

Wild strains can however naturally undergo point mutations within their genetic material (i.e. within their DNA) without affecting their fermentation performance.

According to the invention, a "bioreactor", also referred to as "fermenter", is an item of equipment for the propagation of fermentative microorganisms capable of producing molecules (solvents or other organic compounds) of interest. Fermentation in a bioreactor thus enables, in the presence of C5 and/or C6 sugars, growth of the microorganism used, with control of key parameters such as pH, stirring and temperature of the fermentation (or fermentative) medium, also referred to as reaction medium, and the production of the targeted solvents.

The fermentation step according to the invention therefore consists in growing the microorganisms and recovering a reaction effluent comprising the fermentation broth containing an aqueous solution comprising a mixture of isopropanol, n-butanol and ethanol. According to the invention, the volume of a bioreactor corresponds to the working volume of said bioreactor.

According to the invention, the term "solvents" denotes all of the alcohol and ketone compounds produced by fermentation. More particularly, the term "solvents" denotes the isopropanol, butanol, ethanol and acetone mixture produced during the IBE fermentation carried out in the process according to the invention.

According to the present invention, the expression "between . . . and . . . " means that the limit values of the interval are included in the described range of values. If such were not the case and if the limiting values were not included in the range described, such a clarification will be introduced by the present invention.

For the purposes of the present invention, the various ranges of parameters for a given step, such as the pressure and temperature ranges, may be used alone or in combination. For example, within the meaning of the present invention, a range of preferred pressure values can be combined with a range of more preferred temperature values.

In the text hereinbelow, specific and/or preferred embodiments of the invention may be described. They can be implemented separately or combined together, without limitation of combination when this is technically feasible.

The invention thus relates to a process for producing alcohols comprising, preferably consisting of, the following steps:

a. a step of IBE-type fermentation using a reaction section comprising at least one bioreactor which contains a natural strain microorganism, said reaction section being fed at least with an aqueous solution of C5 and/or C6 sugars and a recycled acetone stream, in order to produce fermentation gases and a fermentation broth containing fermentation products comprising butanol, ethanol, isopropanol and acetone;

b. a step of recovering the fermentation products, in order to obtain a stream of fermentation products;

c. a step of treating the stream of fermentation products from step b) using an acetone separation section in order to produce at least an acetone effluent and an aqueous alcohol effluent;

d. a step of recycling the acetone which uses at least one transfer section in order to recycle at least one faction of the acetone effluent from step c) to step a), said at least one fraction of the acetone effluent which is transferred constituting said recycled acetone stream which feeds the reaction section.

Feedstock

According to the invention, the process is fed with an aqueous solution of C5 and/or C6 sugars.

Said aqueous solution of C5 and/or C6 sugars can have various origins. It advantageously originates from the treatment of a renewable source. This renewable source can be of the lignocellulosic biomass type which notably comprises ligneous substrates (deciduous plants and coniferous plants), agricultural byproducts (straw) or byproducts from industries generating lignocellulosic waste (agrifood or paper industries). The aqueous solution of sugars can also be obtained from sugar-producing plants, for instance sugar beet and sugarcane, or from starchy plants such as corn or wheat.

Any C5 sugar naturally present in the various lignocellulosic biomasses (monocotyledons or dicotyledons) used for the biological biofuel production can be fermented by the process according to the invention. Preferably, the C5 sugars are chosen from xylose and arabinose. Any C6 sugar can also be fermented by the process according to the invention. Preferably, the C6 sugars are chosen from glucose, mannose, galactose. More preferably, the C6 sugar is glucose.

Advantageously, the C5 and/or C6 sugars are solubilized in said aqueous solution of sugars. The concentration of C5 and/or C6 sugars in said aqueous solution of sugars is between 1 and 900 g/l, preferably between 10 and 600 g/l, preferentially between 20 and 500 g/l, very preferably between 25 and 150 g/l. Preferably, the aqueous solution of C5 and/or C6 sugars is a liquid solution.

Step a)

In accordance with the invention, the process for producing alcohols comprises a fermentation step a) using a reaction section which itself comprises at least one bioreactor in which the IBE fermentation is carried out in the presence of a natural microorganism.

Said natural microorganism is a strain of *Clostridium* capable of naturally producing the alcohols isopropanol, n-butanol (also referred to as butanol according to the invention) and ethanol from C5 and/or C6 sugars.

According to one or more embodiments, the fermentation system, also referred to as bacterial biomass, is produced at least by (and/or comprises) a microorganism, or bacterium, belonging to the genus *Clostridium* and capable of producing isopropanol in the wild state, in particular capable of carrying out IBE fermentation in the wild state and advantageously selected from a *C. beijerinckii* bacterium, a *C. diolis* bacterium, a *C. puniceum* bacterium, a *C. aurantibutyricum* bacterium, a *C. butyricum* bacterium, a *C. saccharoperbutylacetonicum* bacterium, a *C. botulinum* bacterium, a *C. drakei* bacterium, a *C. scatologenes* bacterium, a *C. perfringens* bacterium and a *C. tunisiense* bacterium, preferably from a *C. beijerinckii* bacterium, a *C. diolis* bacterium, a *C. puniceum* bacterium, a *C. aurantibutyricum* bacterium and a *C. saccharoperbutylacetonicum* bacterium. Preferably, the microorganism used is a *C. beijerinckii* bacterium, preferably a subclade of *C. beijerinckii* selected from DSM 6423, LMG 7814, LMG 7815, NRRL B-593, NCCB 27006, a *C. aurantibutyricum* DSZM 793 or ATCC 17777 bacterium, or a subclade of such a *C. beijerinckii* or *C. aurantibutyricum* bacterium having at least 90%, 95%, 96%, 97%, 98% or 99% identity with the DSM 6423 strain (cf. as disclosed above).

Said reaction section may comprise one or more bioreactors, preferably at least two bioreactors, preferentially at least five bioreactors. Advantageously, said reaction section comprises at most thirty bioreactors, preferably at most twenty bioreactors, preferentially at most ten bioreactors. Each bioreactor comprises said natural microorganism. When the reaction section comprises several bioreactors, the bioreactors operate in parallel.

Said reaction section is fed with an aqueous solution of C5 and/or C6 sugars. Advantageously, said aqueous solution is in liquid form. When said reaction section comprises several bioreactors, said aqueous solution of C5 and/or C6 sugars can be divided into as many aqueous sugar solution feed streams as there are bioreactors present in said reaction section.

Said reaction section is also fed with a recycled acetone stream, advantageously from step d) of the process according to the invention. Advantageously, said recycled acetone stream is in liquid form. Said recycled acetone stream can be introduced directly into said bioreactor(s) or into a mixer located upstream of said bioreactor in which it is mixed with said aqueous solution of C5 and/or C6 sugars before being introduced into said bioreactor(s). When said reaction section comprises several bioreactors, said recycled acetone stream can be divided into as many recycled acetone feed streams as there are bioreactors present in said reaction section.

Said reaction section can also be optionally fed with an exogenous acetone stream. Advantageously, said exogenous acetone stream which optionally feeds the reaction section is in liquid form. Said exogenous acetone stream can be mixed with the recycled acetone stream C6 before being introduced into said bioreactor(s) or can feed said bioreactor(s) directly.

Said exogenous acetone stream which optionally feeds the reaction section, is a biocompatible acetone stream, resulting from at least one process other than the process according to the invention. Said exogenous acetone stream may originate, at least in part, from another fermentation process, for example that performs an ABE fermentation, or from a "chemical" process, that is to say a process that does not perform any fermentation. In the latter case, the acetone produced by the chemical process is directly biocompatible, that is to say contains no poison for the microorganisms used in step a) of the process according to the invention, or is treated prior to being introduced into the reaction section of step a) to make it biocompatible.

Advantageously, the reaction section of step a) is fed with said recycled acetone stream and optionally said exogenous acetone stream, at flow rates that are adjusted so that the concentration of acetone feeding the reaction section of step a) is less than or equal to 10 g/l, preferably less than or equal to 5 g/l, preferentially less than or equal to 2 g/l and preferably strictly greater than 0, preferentially greater than or equal to 0.01 g/l, preferably greater than or equal to 0.1 g/l, relative to all of the liquid streams feeding the reaction section of step a), that is to say relative to the aqueous solution of C5 and/or C6 sugars, the recycled acetone stream and optionally the exogenous acetone stream. The concentration of acetone feeding the reaction section of step a) is defined as being the weight amount of total acetone entering the reaction section of step a), that is to say provided by the recycled acetone stream and optionally the exogenous acetone stream, relative to the total volume of the streams feeding the reaction section of step a), that is to say relative to the sum of the liquid streams composed of the aqueous sugar solution stream, the recycled acetone stream and optionally the exogenous acetone stream, expressed by volume.

Advantageously, the fermentation carried out in the reaction section is performed at a temperature of between 25° C. and 40° C., preferably between 30° C. and 37° C., preferably at 34° C. Preferably, the fermentation is carried out at a pH of between 4.0 and 7.0, preferably between 4.5 and 6.0. Advantageously, the reaction section of step a) is operated at atmospheric pressure.

According to one particular embodiment of the invention, the fermentation can be carried out in batch mode, that is to say with an initial feed and without intermediate feed and/or without continuous feed, in particular of aqueous sugar solution, of said recycled acetone stream, optionally from the preceding batch or batches, and optionally of an exogenous acetone stream. In other words, in this embodiment, the fermentation is carried out in the bioreactor(s) which is/are advantageously closed for the liquid phase (but open for the outgoing gas phase), for a period of between 30 and 150 hours which advantageously corresponds to the duration of a batch. Preferably, the working volume of the bioreactor(s) is between 10 and 500 m³. The amount of aqueous solution of C5 and/or C6 sugars initially introduced into the (or each) bioreactor, preferably at a concentration of between 1 and 900 g/l, preferably between 10 and 600 g/l, preferably between 20 and 500 g/l and even more preferably between 30 g/l and 90 g/l, and in particular between 40 g/l and 60 g/l, corresponds to half the working volume of the bioreactor considered, and advantageously corresponds to the fermentation medium of said bioreactor. The amount of microorganisms introduced per batch and per bioreactor corresponds to a volume of a cell (or bacteria) culture medium at the maximum growth rate and such that said volume of the culture medium is between 2% and 10% of the volume of the fermentation medium (or reaction volume). Continuous stirring is maintained to homogenize the reaction medium.

According to a second particular embodiment of the invention, the fermentation can be carried out in "semi-continuous" or "fed-batch" mode. In this embodiment, the aqueous sugar solution and advantageously the acetone stream are advantageously introduced into the bioreactor(s), for one portion at the start of a batch and for another portion added in the course of the batch in the bioreactor(s). A batch denotes, according to the knowledge of those skilled in the art, advantageously the time for carrying out the fermentation between two emptyings of the bioreactor(s) and the operations that take place during this time. A batch lasts preferably between 20 and 200 hours, preferably between 30 and 150 hours. Preferably, the working volume of the bioreactor(s) is between 10 and 500 m³. Preferably, the (or each) bioreactor is initially fed with an amount of aqueous solution of C5 and/or C6 sugars, preferably with a sugar concentration of between 30 g/l and 90 g/l, preferably between 40 g/l and 60 g/l, which corresponds to a volume preferably equal to half the working volume of the (each) bioreactor. During the fermentation, each bioreactor is fed, advantageously continuously or by pulse-wise, with an aqueous solution of C5 and/or C6 sugars, preferably with a sugar concentration of between 500 and 800 g/l, at a flow rate advantageously between 10 and 5000 I/h, preferably between 20 and 2500 I/h. The amount of microorganisms introduced per batch and per bioreactor corresponds to a volume of a cell (or bacteria) culture medium at the maximum growth rate and such that said volume of the culture medium is between 2% and 10% of the volume of the fermentation medium (or reaction volume). Continuous stirring is maintained to homogenize the reaction medium, in each bioreactor. A withdrawal of the butanol produced, in liquid or gas form, continuously or pulse-wise, can then be carried out in each bioreactor, the objective of this technique being to eliminate the butanol, which is toxic to microorganisms, as it is produced by the strain. This technique is referred to as ISPR for In Situ Product Recovery and is well known to those skilled in the art (cf. Outram V. et al. "A comparison of the energy use of in situ product recovery techniques for the Acetone Butanol Ethanol fermentation", Bioresource Technology, 2016, 220, 590-600).

When the fermentation is carried out in batch mode or in semi-continuous (or fed-batch) mode, the term "stream" denotes the amounts introduced or leaving the bioreactor(s), per batch.

According to a third particular embodiment of the invention, the fermentation can be carried out in "simple continuous" mode, also referred to as continuous mode with free cells. The bioreactor(s) is (are) then fed continuously with the aqueous sugar solution and the recycled acetone stream, and optionally an exogenous acetone stream. The feed flow rate of said aqueous solution of C5 and/or C6 sugars, at a concentration advantageously between 1 to 900 g/l, preferentially between 10 and 600 g/l, preferably between 20 and 500 g/l, very preferably between 25 and 150 g/l, is adjusted so that the dilution rate in the bioreactor(s), expressed in $h^{-1}$ and corresponding to the inverse of the residence time (that is to say to the flow rate of said aqueous solution of C5 and/or C6 sugars divided by the volume, that is to say the working volume, of the bioreactors), as well known to those skilled in the art, is between 0.01 and 0.05 $h^{-1}$, preferably between 0.0125 and 0.033 $h^{-1}$. The feed flow rate of said recycled acetone stream, and optionally said exogenous acetone stream, is adjusted as indicated above, so that the concentration of acetone feeding the bioreactor relative to the sum of the liquid streams feeding the bioreactor (that is to say the aqueous sugar solution, the recycled acetone stream and optionally the exogenous acetone stream) is less than or equal to 10 g/l, preferably less than or equal to 5 g/l, preferentially less than or equal to 2 g/l, and preferably strictly greater than 0, preferentially greater than or equal to 0.01 g/l, preferably greater than or equal to 0.1 g/l. Advantageously, in the case of a fermentation carried out in simple continuous mode, the microorganism concentration in the reaction medium, also referred to as fermentation medium, is between $10^8$ and $10^{11}$ cells/ml of reaction medium, preferably between $10^9$ and $10^{10}$ cells/ml of reaction medium. Continuous stirring of the reaction medium in the bioreactor (s) is advantageously maintained to homogenize said reaction medium. In this embodiment, the microorganisms and the products formed are withdrawn, continuously or pulse-wise, from the bioreactor(s). An ISPR technique, as described above, can also be applied to eliminate butanol, which is toxic to bacteria.

According to another particular embodiment of the invention, the fermentation can be carried out in "supported continuous" mode, also referred to as confined continuous mode or continuous mode with immobilized cells. The microorganisms then form a film, or biofilm, on a solid support, for example composed of a porous inorganic material, such as clays, a metal foam, a polymeric foam, in particular a polyurethane foam, the polyurethane foam being preferred (cf. FR 3 086 670). Advantageously, in the case of a fermentation carried out in supported continuous mode, the microorganism concentration is between $10^7$ and $10^{10}$ cells/cm³ of solid support, preferably between $10^8$ and $10^9$ cells/cm³ of solid support. The inoculated solid support, that is to say the solid support containing the microorganism biofilm, preferably the inoculated polyurethane foam, is then placed in the or each bioreactor so that the volume of inoculated solid support represents preferably between 1% and 50% of the working volume of the bioreactor, preferably between 5% and 30% of the working volume of the bioreactor. The bioreactor(s) is (are) then fed continuously with the aqueous solution of C5 and/or C6 sugars, at a concentration advantageously between 1 and 900 g/l, preferentially between 10 and 600 g/l, preferably between 20 and 500 g/l, very preferably between 25 and 150 g/l, and the recycled acetone stream, and optionally an exogenous acetone stream. The flow rate for feeding the bioreactor(s) with said aqueous solution of C5 and/or C6 sugars is adjusted so that the dilution rate, expressed in $h^{-1}$ and corresponding to the inverse of the residence time (that is to say to the flow rate of said aqueous solution of C5 and/or C6 sugars divided by the volume, that is to say the working volume, of the bioreactors), as well known to those skilled in the art, is between 0.01 and 0.40 $h^{-1}$, preferably between 0.015 and 0.30 $h^{-1}$, preferably between 0.02 and 0.20 $h^{-1}$. The feed flow rate of said recycled acetone stream, and optionally said exogenous acetone stream, is adjusted as indicated above, so that the concentration of acetone feeding the bioreactor relative to all of the liquid streams feeding the bioreactor (that is to say the aqueous sugar solution, the recycled acetone stream and optionally the exogenous acetone stream) is less than or equal to 10 g/l, preferably less than or equal to 5 g/l, preferentially less than or equal to 2 g/l, and preferably strictly greater than 0, preferentially greater than or equal to 0.01 g/l, preferably greater than or equal to 0.1 g/l. Continuous stirring of the reaction medium in the bioreactor(s) is advantageously maintained to homogenize said reaction medium. In this embodiment, the microorganisms and the products formed are withdrawn, continuously or pulse-wise, from the bioreactor(s). An ISPR technique, as described above, can also be applied to eliminate butanol, which is toxic to bacteria.

Preferably, the fermentation is carried out in simple continuous mode or continuous mode with cell immobilization, and preferentially in continuous mode with cell immobilization.

Said step a) enables the production of fermentation gases, in particular comprising carbon dioxide ($CO_2$) and hydrogen, and a fermentation broth containing fermentation products comprising butanol, ethanol, isopropanol and acetone.
Step b)

In accordance with the invention, the process for producing alcohols comprises a step b) of recovering the fermentation products generated in step a), in order to obtain a stream of fermentation products.

This step advantageously consists at least in separating the fermentation products, comprising in particular butanol, ethanol, isopropanol and acetone as a mixture with water, from the fermentation broth and the fermentation gases.

This separation can be carried out by any method known to those skilled in the art. For example, the process for recovering alcohols in a fermenter described in WO 2018/001628 can very particularly be used in this step b).

Said stream of fermentation products obtained at the end of step b) comprises in particular isopropanol, n-butanol, ethanol and acetone, as a mixture with water.
Step c)

In accordance with the invention, the process for producing alcohols comprises a step c) of treating the stream of fermentation products resulting from step b). Said step c) uses at least one acetone separation section in order to produce at least an acetone effluent and an aqueous alcohol effluent. Said aqueous alcohol effluent comprises in particular butanol, ethanol and isopropanol.

The separation of the acetone from the stream of fermentation products can be carried out according to any method known to those skilled in the art, such as for example by distillation(s), fractionation(s), etc. It can in particular carry out a succession of distillations. Thus in a particular embodiment of the invention, step c) carries out, in said acetone separation section:

c-1) a distillation of the stream of fermentation products from step b) in a beer column in order to obtain a stream of water at the bottom of said beer column and an aqueous mixture of solvents at the top of the beer column, c-2) a distillation of the aqueous mixture of solvents in a distillation column, in order to obtain said acetone effluent at the top of the column and said aqueous alcohol effluent at the bottom of the column.

The aqueous mixture of solvents extracted at the top of the beer column of step c-1) of this particular embodiment comprises water, butanol, in particular n-butanol, ethanol, isopropanol and acetone. Said beer column of step c-1) may advantageously be equipped with a reboiling system, preferably by recompression of overhead vapours. It may also comprise a reflux recycle system.

The aqueous mixture of solvents, extracted at the top of the beer column of step c-1) of the particular embodiment, is then sent to a distillation column, also referred to as an "acetone column". The role of the acetone column of step c-2) is to separate the acetone from the alcohol stream, the acetone being extracted at the top of the column, and to produce said aqueous alcohol effluent, advantageously concentrated in isopropanol-butanol-ethanol, which is withdrawn at the bottom of said acetone column.

Advantageously, the acetone effluent obtained at the end of step c) has an acetone concentration of greater than or equal to 95% by weight, preferably greater than or equal to 98% by weight, preferably greater than or equal to 99.5% by weight relative to the weight of said acetone effluent The aqueous alcohol effluent itself comprises water and a mixture of alcohols, said alcohols being those advantageously produced during the IBE fermentation, in particular n-butanol (referred to as butanol), ethanol and isopropanol.

Step c) may optionally further comprise an alcohol separation section. Said optional alcohol separation section comprises a distillation column, fed with the aqueous alcohol effluent resulting from the acetone separation section. It makes it possible to separate at least one butanol effluent and one aqueous-alcoholic effluent comprising ethanol and isopropanol.
Step d)

In accordance with the invention, the process for producing alcohols comprises a step d) of recycling the acetone. This acetone recycling step uses at least one transfer section to recycle at least one fraction of the acetone effluent from step c) to step a). Said fraction of the acetone effluent which is recycled to step a) constitutes the recycled acetone stream which feeds the reaction section of said step a) of the process according to the invention.

The process according to the invention can operate in continuous, batch or semi-continuous mode, as described above. Preferably, the process operates in continuous mode, and preferably in confined continuous mode.

The process according to the invention thus makes it possible to reintegrate the acetone co-produced in the fermentation medium, into the bioreactor, in order for it to be reassimilated by the microorganisms and to convert it into isopropanol. Since the reassimilation of acetone is virtually complete, the isopropanol yield is improved, a gain of between 4% and 6% by weight depending on the strains of *Clostridium* used, compared to a process using the same strain and the same number of natural microorganisms but without the system for recycling and reassimilating the co-produced acetone. The process according to the invention therefore enables an increase in the overall yield of conversion of sugars to alcohols compared to an IBE fermentation process without upgrading of the acetone co-product. The process according to the present invention also makes it possible to upgrade acetone exogenous to said process by converting it to isopropanol, and in particular at low pressures compared to a conventional process using by chemical means.

The figures incorporated in the present description and the examples that follow are presented as nonlimiting illustrations of the process according to the invention.

According to the invention, in particular in the examples, the unit of weight "tonne" is written as "t", the unit of weight "gram" is written as "g", and the unit of time "hour" is written as "h".

LIST OF FIGURES

FIG. 1 schematically represents a particular arrangement of the process according to the invention. An aqueous solution of C5 and/or C6 sugars (1) feeds a reaction section (R1) comprising at least one bioreactor. Said bioreactor comprises a microorganism that naturally converts sugars to isopropanol, butanol and ethanol alcohols. The fermentation products (2) obtained after IBE fermentation of the sugars are recovered and introduced into an acetone separation section (C) which separates an acetone effluent (3) which is entirely recycled to the reaction section (R1) and an aqueous alcohol effluent (4) comprising isopropanol, butanol and ethanol.

Figure 2:
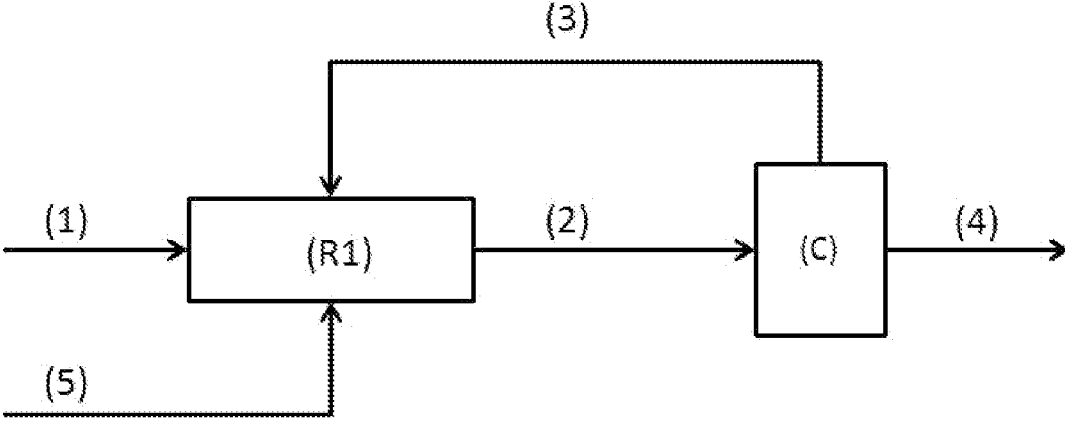

FIG. 2 represents another particular arrangement of the process according to the invention. The process depicted in FIG. 2 further comprises, compared to the process depicted in FIG. 1, an exogenous acetone feed (5) such that the total concentration of acetone feeding the section (R1) is less than or equal to 10 g/l, preferably less than or equal to 5 g/l, preferably less than or equal to 2 g/l, and preferably strictly greater than 0, preferentially greater than or equal to 0.01 g/l, preferably greater than or equal to 0.1 g/l, relative to all of the streams feeding said section (R1).

EXAMPLES

The examples below are constructed from the results of laboratory tests carried out in the presence of microorganisms of the genus *Clostridium* and in particular with the DSM6423 strain which naturally produces, from C5 and/or C6 sugars, solvents with the following distribution of Isopropanol/Butanol/Ethanol/Acetone: 36%/60%/2%/2%, expressed as weight percentages.

Example 1 (not in Accordance)

Example 1 illustrates an IBE fermentation process in the presence of the *Clostridium beijerinckii* DSM6423 strain, without a system for recycling the co-produced acetone. It is a process in accordance with the prior art.

The fermentation production unit uses a fermentation unit comprising 4 fermenters which treats a 62.5 g/l aqueous solution of glucose (C6 sugar). The total working volume of the fermenters of the fermentation unit is 14 000 m³. The sugar consumption of the plant is around 125 000 t/year of glucose, corresponding to a flow rate of 250 000 l/h of aqueous glucose solution, i.e., a dilution rate of 0.022 h⁻¹. The fermenters operate at 37° C., at atmospheric pressure and at a pH of between 4.5 and 6. The unit operates in simple continuous mode. The number of microorganisms is between $10^9$ and $10^{10}$ cells/ml of reaction medium.

The production unit also comprises a unit for treating the solvents produced, in particular an acetone separation unit, comprising a beer column followed by an acetone column, in order to separate the acetone produced from the alcohols.

The production unit produces 40 000 tons of solvents per year.

Table 1 summarizes the amounts of the various solvents produced.

TABLE 1

| Solvents | Amounts produced (t/year) |
|---|---|
| Acetone | 800.0 |
| Ethanol | 800.0 |
| Isopropanol | 14 400.0 |
| Butanol | 24 000.0 |

The total yield of glucose to solvents (acetone+ethanol+isopropanol+butanol) is 0.320 kg/kg (i.e. kg of solvents produced per kg of glucose consumed) and the conversion rate of glucose to alcohols (ethanol+isopropanol+butanol) is 0.314 kg/kg.

Example 2 (in Accordance)

Example 2 illustrates a process according to the invention. Example 2 specifically illustrates an IBE fermentation process in the presence of the *Clostridium beijerinckii* DSM6423 strain, with a system for recycling the co-produced acetone.

The parameters and operating conditions of the process described in example 1 are used.

The production unit further comprises a system for recycling the acetone that is co-produced and separated in the dedicated separation unit. A stream of around 100 000 g/h of acetone is thus produced and continuously recycled to the fermenters. All the separated acetone effluent is recycled to the fermentation unit.

The acetone concentration of all the streams feeding the bioreactor is 0.4 g/l throughout the production.

Table 2 shows the amounts of the various solvents produced, by the process described in example 2.

TABLE 2

| Solvents | Amounts produced (t/year) |
|---|---|
| Acetone | 80 |
| Ethanol | 800 |
| Isopropanol | 15 120 |
| Butanol | 24 000.0 |

The total yield of glucose to solvents (acetone+ethanol+isopropanol+butanol) is still 0.320 kg of solvents per kg of glucose but the conversion rate of glucose to alcohols (ethanol+isopropanol+butanol), according to the process of example 2, is 0.319 kg/kg, instead of 0.314 kg/kg, obtained by the process of example 1 not in accordance with the invention. The *Clostridium beijerinckii* DSM6423 strain present in the fermenters of the fermentation unit assimilated the reintroduced acetone and converted it to isopropanol with a yield of acetone to isopropanol of 90% by weight (90%=100×(15 120−14 400)/800).

The increase in isopropanol production is around 5.0% by weight (5.0%=(15120−14400)/14400) compared to the process described in example 1 (not in accordance with the invention) which does not comprise a system for upgrading the acetone.

The invention claimed is:

1. A process for producing alcohols comprising the following steps:
   a. a fermentation step using a reaction section comprising at least one bioreactor wherein an Isopropanol-Butanol-Ethanol-type fermentation is carried out in the presence of a strain of *Clostridium* that naturally synthesizes, during fermentation, at least one secondary alcohol dehydrogenase (sadh) enzyme that enables the conversion of acetone to isopropanol in the presence of nicotinamide adenine dinucleotide phosphate (NADPH), said reaction section being fed at least with an aqueous solution of C5 or C6 sugars or a combination thereof and a recycled acetone stream, in order to produce fermentation gases and a fermentation broth containing fermentation products comprising butanol, ethanol, isopropanol and acetone;
   b. a step of recovering the fermentation products, in order to obtain a stream of fermentation products;
   c. a step of treating the stream of fermentation products from step b) using an acetone separation section in order to produce at least an acetone effluent having an acetone concentration of greater than or equal to 95% by weight, relative to the weight of said acetone effluent, and an aqueous alcohol effluent;
   d. a step of recycling the acetone which uses at least one transfer section in order to recycle at least one fraction of the acetone effluent from step c) to step a), said at least one fraction of the acetone effluent which is transferred constituting said recycled acetone stream which feeds the reaction section of step a).

2. The process as claimed in claim 1, wherein the reaction section of step a) is additionally fed with an exogenous acetone stream.

3. The process as claimed in claim 2, wherein the reaction section of step a) is fed with said recycled acetone stream and said exogenous acetone stream, at flow rates that are adjusted so that the concentration of acetone in all of the liquid streams, composed of the aqueous solution of C5 or C6 sugars or a combination thereof, the recycled acetone stream and the exogenous acetone stream, feeding the reaction section of step a) is less than or equal to 10 g/l.

4. The process as claimed in claim 1, wherein the fermentation carried out in the reaction section of step a) is carried out at a temperature of between 25° C. and 40° C.

5. The process as claimed in claim 1, wherein the fermentation carried out in the reaction section of step a) is carried out at a pH of between 4 and 7.

6. The process as claimed in claim 1, wherein the reaction section of step a) is operated at atmospheric pressure.

7. The process as claimed in claim 1, wherein the reaction section includes at least two bioreactors, and at most thirty bioreactors.

8. The process as claimed in claim 1, wherein the fermentation is carried out in batch mode for a period of between 30 and 150 hours.

9. The process as claimed in claim 1, wherein the fermentation is carried out in semi-continuous mode for 20 to 200 hours.

10. The process as claimed in claim 1, wherein the fermentation is carried out in simple continuous mode, the concentration of *Clostridium* strain in the reaction medium is between $10^8$ and $10^{11}$ cells/ml of reaction medium.

11. The process as claimed in claim 1, wherein the fermentation is carried out in supported continuous mode, the *Clostridium* strain being in the form of a biofilm on a solid support and the concentration of *Clostridium* strain in the reaction medium is between $10^7$ and $10^{10}$ cells/cm³ of solid support.

12. The process as claimed in claim 1, wherein step c) carries out, in said acetone separation section:

c-1) a distillation of the stream of fermentation products from step b) in a beer column in order to obtain a stream of water at the bottom of said beer column and an aqueous mixture of solvents at the top of the beer column, c-2) a distillation of the aqueous mixture of solvents in a distillation column, in order to obtain said acetone effluent at the top of the column and said aqueous alcohol effluent at the bottom of the column.

13. The process as claimed in claim 1, wherein the reaction section of step a) is fed with said recycled acetone stream at a flow rate that is adjusted so that the concentration of acetone in all of the liquid streams, composed of the aqueous solution of C5 or C6 sugars or a combination thereof, and the recycled acetone stream, feeding the reaction section of step a) is less than or equal to 10 g/l.

14. The process as claimed in claim 1, wherein the strain of *Clostridium* is a *C. beijerinckii* bacterium, a *C. diolis* bacterium, a *C. puniceum* bacterium, a *C. aurantibutyricum* bacterium, a *C. butyricum* bacterium, a *C. saccharoperbutylacetonicum* bacterium, a *C. botulinum* bacterium, a *C. drakei* bacterium, a *C. scatologenes* bacterium, a *C. perfringens* bacterium or a *C. tunisiense* bacterium.

15. The process as claimed in claim 1, wherein the strain of *Clostridium* is a *C. beijerinckii* bacterium DSM 6423, LMG 7814, LMG 7815, NRRL B-593 or NCCB 27006, or a *C. aurantibutyricum* DSZM 793 or ATCC 17777 bacterium.

16. A process for producing alcohols comprising the following steps:

a. a fermentation step using a reaction section comprising at least one bioreactor wherein an Isopropanol-Butanol-Ethanol-type fermentation is carried out in the presence of *Clostridium beijerinckii* DSM6423, said reaction section being fed at least with an aqueous solution of C5 or C6 sugars or a combination thereof and a recycled acetone stream, in order to produce fermentation gases and a fermentation broth containing fermentation products comprising butanol, ethanol, isopropanol and acetone;

b. a step of recovering the fermentation products, in order to obtain a stream of fermentation products;

c. a step of treating the stream of fermentation products from step b) using an acetone separation section in order to produce at least an acetone effluent having an acetone concentration of greater than or equal to 95% by weight, relative to the weight of said acetone effluent, and an aqueous alcohol effluent;

d. a step of recycling the acetone which uses at least one transfer section in order to recycle at least one faction of the acetone effluent from step c) to step a), said at least one fraction of the acetone effluent which is transferred constituting said recycled acetone stream which feeds the reaction section of step a).

17. The process as claimed in claim 16, wherein the reaction section of step a) is additionally fed with an exogenous acetone stream.

* * * * *